United States Patent [19]
Bishop et al.

[11] Patent Number: 5,972,917
[45] Date of Patent: Oct. 26, 1999

[54] 1 α-HYDROXY-25-ENE-VITAMIN D, ANALOGS AND USES THEREOF

[76] Inventors: Charles W. Bishop, 5 LaPointe Ter., Madison, Wis. 53719; Joyce C. Knutson, 24 N. Prospect Ave., Madison, Wis. 53705; Stephen Strugnell, 2622 Dahle St., Madison, Wis. 53704

[21] Appl. No.: 09/087,439

[22] Filed: May 29, 1998

[51] Int. Cl.$^6$ .......................... A61K 31/59; C07C 401/00
[52] U.S. Cl. ............................................ 514/167; 552/653
[58] Field of Search ............................. 514/167; 552/653

[56] References Cited

U.S. PATENT DOCUMENTS

| | | | |
|---|---|---|---|
| 4,195,027 | 3/1980 | DeLuca et al. | 260/397.2 |
| 4,202,829 | 5/1980 | DeLuca et al. | 260/387.2 |
| 4,225,596 | 9/1980 | DeLuca | 424/236 |
| 4,234,495 | 11/1980 | DeLuca et al. | 260/397.2 |
| 4,260,549 | 4/1981 | DeLuca et al. | 590/397.2 |
| 4,341,774 | 7/1982 | Aoki et al. | 424/236 |
| 4,388,243 | 6/1983 | Nishikawa et al. | 260/397.2 |
| 4,391,802 | 7/1983 | Suda et al. | 424/236 |
| 4,554,106 | 11/1985 | DeLuca et al. | 260/397.2 |
| 4,555,364 | 11/1985 | DeLuca et al. | 260/397.2 |
| 4,652,405 | 3/1987 | Pavtridge et al. | 260/397.1 |
| 4,689,180 | 8/1987 | DeLuca et al. | 260/397.2 |
| 4,749,710 | 6/1988 | Truitt et al. | 514/167 |
| 4,891,364 | 1/1990 | Kubodera et al. | 514/167 |
| 5,035,783 | 7/1991 | Goethals et al. | 204/157.67 |
| 5,063,221 | 11/1991 | Nishii et al. | 514/167 |
| 5,098,899 | 3/1992 | Gilbert et al. | 514/167 |
| 5,190,935 | 3/1993 | Binderup et al. | 514/167 |
| 5,206,229 | 4/1993 | Calverley et al. | 514/167 |
| 5,250,523 | 10/1993 | DeLuca et al. | 514/167 |
| 5,252,191 | 10/1993 | Pauli et al. | 204/157.67 |
| 5,304,291 | 4/1994 | Bout et al. | 204/156.7 |
| 5,374,629 | 12/1994 | Calverley et al. | 514/167 |
| 5,449,668 | 9/1995 | Sestelo et al. | 514/167 |
| 5,518,725 | 5/1996 | Daynes et al. | 424/212.1 |
| 5,540,919 | 7/1996 | Daynes et al. | 424/85.2 |
| 5,559,107 | 9/1996 | Gates et al. | 514/167 |
| 5,561,123 | 10/1996 | DeLuca et al. | 514/167 |
| 5,562,910 | 10/1996 | Daynes et al. | 424/212.1 |
| 5,585,368 | 12/1996 | Steinmeyer et al. | 514/167 |
| 5,589,471 | 12/1996 | Hansen et al. | 514/167 |
| 5,665,387 | 9/1997 | Mathieu et al. | 424/455 |
| 5,700,791 | 12/1997 | Steinmeyer et al. | 514/167 |
| 5,710,142 | 1/1998 | Calverley et al. | 514/169 |
| 5,710,294 | 1/1998 | DeLuca et al. | 552/397.2 |
| 5,716,946 | 2/1998 | DeLuca et al. | 514/167 |
| 5,750,517 | 5/1998 | Baggiolini et al. | 514/167 |
| 5,750,746 | 5/1998 | DeLuca et al. | 552/653 |

OTHER PUBLICATIONS

M. F. Holick et al., *Proc. Natl. Acad. Sci. USA* 68, 803–804 (1971).
G. Jones et al., *Biochemistry* 14, 1250–1256 (1975).
M. F. Holick et al., *Science* 180, 190, 191 (1973).
H. Y. Lam et al., *Science* 486, 1038–1040 (1974).
S. M. Ott, C. H. Chesnut, *Annals of Int. Med.* 1989, 110:267–274.
J. C. Gallagher et al., *Annals of Int. Med.* 1990, 113:649–655.
J. Aloia et al., *Amer. J. Med.* 84:401–08 (1988).
M. Shiraki et al., *Endocrinol.* Japan 32, 305–315 (1985).
G. F. Jensen et al., *Clin. Endocrinol.* 16, 515–524 (1982).
C. Christiansen et al., *Eur. J. Clin. Invest.* 11, 305–309 (1981).
O. H. Sorensen et al., *Clin. Endocrinol.* 7, 169S–175S (1977).
H. Orimo et al., *Bone and Mineral* 3, 47–52 (1987).
G. Sjoden et al., *J. Nutr.* 114, 2043–2046 (1984).
G. Sjoden et al., *Proc. Soc. Exp. Biol. Med.* 178, 432–436 (1985).
*The Merck Index*, 11th ed. (1989) p. 9932.
*J. Bone Min. Res.*; 1994; 9:607–614.
*Biochem. J.*, vol. 310, No. 1 (Aug. 15, 1995) pp. 233–241.
*Endocrinology*, vol. 136, No. 11 (Nov. 1995) pp. 4749–4753.
Miller et al., 52 *Cancer Res.* (1992) 515–520.
Skowronski et al., 136 *Endocrinology* 20–26 (1995).
Horst, R. L., Koszewski, N. J. and Reinhardt, T. A., *Biochem.*, 29:578–82 (1990).
White et al., 1 *J. Chem. Soc. Perkin Trans* (1993) 759.
Nishigaichi et al. *Chem. Lett.* (1996) 961.
Manchand et al., 60 *J. Org. Chem.* (1995) 6574.
Strugnell et al., *Biochem. J.*, 310: 233–241 (1995).

*Primary Examiner*—Theodore J. Criares
*Attorney, Agent, or Firm*—Michael Best & Friedrich LLP; Teresa J. Welch

[57] ABSTRACT

The invention provides 1α-hydroxyvitamin D compounds in which the C-25 or equivalent position of the C-17 side chain has a double bond and method for their use in the treatment and prophylaxis of hyperparathyroidism and hyperproliferative diseases, and in the modulation of the immune and inflammatory responses as well as the treatment of bone depletive disorders.

19 Claims, 1 Drawing Sheet

1 α-HYDROXY-25-ENE-VITAMIN D, ANALOGS AND USES THEREOF

STATEMENT REGARDING FEDERALLY SPONSORED RESEARCH OR DEVELOPMENT

Not Applicable

BACKGROUND OF THE INVENTION

This invention relates to novel 1α-hydroxyvitamin D compounds and their use in the treatment and prophylaxis of hyperparathyroidism and hyperproliferative diseases, and in the modulation of the immune response as well as the treatment of bone depletive disorders.

Vitamin D has long been established as having an important biological role in bone and mineral metabolism. For example, vitamin D plays a critical role in stimulating calcium absorption and regulating calcium metabolism. The discovery of the active forms of vitamin D in the 1970's (M. F. Holick et al., 68 *Proc. Natl. Acad. Sci. USA* 803–804 (1971); G. Jones et al., 14 *Biochemistry* 1250–1256 (1975)) and active vitamin D analogues (M. F. Holick et al., 180 *Science* 190, 191 (1973); H. Y. Lam et al., 186 *Science* 1038–1040 (1974)), caused much excitement and speculation about the usefulness of these compounds in the treatment of bone depletive disorders.

Animal and early clinical studies examining the effects of these active vitamin D compounds suggested that such agents would be useful in restoring calcium balance. An early clinical study indicated that oral administration of 0.5 μg/day of 1α,25-dihydroxyvitamin $D_3$, the hormonally active form of vitamin $D_3$, to a group of postmenopausal women improved intestinal calcium absorption as well as calcium balance in the women. On this basis, U.S. Pat. No. 4,225,596 ("'596 Patent") described and claimed the use of 1α,25-dihydroxyvitamin $D_3$ for increasing calcium absorption and retention.

The best indicator of the efficacy of vitamin D compounds to prevent or treat depletive bone disorders, however, is bone itself rather than calcium absorption or calcium balance. More recent clinical data indicate that, at the dosage ranges taught in the '596 Patent, 1α,25-dihydroxyvitamin $D_3$ has, at best, modest efficacy in preventing or restoring loss of bone mass or bone mineral content (S. M. Ott and C. H. Chesnut, 110 *Ann. Int. Med.* 267–274 (1989); J. C. Gallagher et al., 113 *Ann. Int. Med.* 649–655 (1990); J. Aloia et al., 84 *Amer. J. Med.* 401–408 (1988)).

These clinical studies with 1α, 25-dihydroxyvitamin $D_3$, and another conducted with 1α-hydroxyvitamin $D_3$ (M. Shiraki et al., 32 *Endocrinol. Japan* 305–315 (1985)) indicate that the capacity of these two vitamin $D_3$ compounds to restore lost bone mass or bone mineral content is dose-related. These studies also indicate, however, that at the dosage ranges required for these agents to be truly effective, toxicity in the form of hypercalcemia and hypercalciuria becomes a major problem. Specifically, attempts to increase the amount of 1α,25-dihydroxyvitamin $D_3$ above 0.5 μg/day have frequently resulted in toxicity. At dosage levels below 0.5 μg/day, clinically significant effects are rarely observed on bone. (See, G. F. Jensen et al., 16 *Clin. Endocrinol.* 515–524 (1982); C. Christiansen et al., 11 *Eur. J. Clin. Invest.* 305–309 (1981)).

Data from clinical studies in Japan, a population that has low calcium intake, indicate that efficacy is found with 1α-hydroxyvitamin $D_3$ when administered at 1 μg/day (M. Shiraki et al., 32 *Endocrinol. Japan.* 305–315 (1985); H. Orimo et al., 3 *Bone and Mineral* 47–52 (1987)). Two μg/day of 1α-hydroxyvitamin $D_3$ were found to have efficacy in increasing bone mass in patients exhibiting senile osteoporosis (O. H. Sorensen et al., 7 *Clin. Endocrinol.* 19S–175S (1977)). At 2 μg/day, however, toxicity with 1α-hydroxyvitamin $D_3$ occurs in approximately 67 percent of the patients, and at 1 μg/day, this percentage is approximately 20 percent. Thus, these 1α-hydroxylated vitamin $D_3$ compounds can produce dangerously elevated blood calcium levels due to their inherent calcemic activity.

Due to this toxicity, 1-hydroxylated vitamin $D_3$ compounds can only be administered at oral dosages that are, at best, modestly beneficial in preventing or treating loss of bone or bone mineral content. Indeed, Aloia recommends that alternative routes of administration be sought which might avoid the toxicity problems and allow higher dosage levels to be achieved. (J. Aloia et al., 84 *Amer. J. Med.* 401–408 (1988).) Yet, despite reported toxicities of 1α-hydroxyvitamin $D_3$ and 1α,25-dihydroxyvitamin $D_3$, these two compounds remain the drugs of choice for many bone depletive disease treatments.

These two drugs also remain the only approved forms of 1α-hydroxylated vitamin D for treating or preventing hyperparathyroidism which occurs secondary to end stage renal disease, although both drugs are not currently approved in all major pharmaceutical markets. Hyperparathyroidism is a generalized disorder resulting from excessive secretion of parathyroid hormone (PTH) by one or more parathyroid glands. It is thus characterized by elevated blood levels of parathyroid hormone. Typically, one or more parathyroid glands reveal a marked enlargement. In the case of primary hyperparathyroidism, the glandular enlargement is usually due to a neoplasm or tumor. In the case of secondary hyperparathyroidism, the parathyroid gland hyperplasia typically occurs because of resistance to the metabolic actions of the hormone. Secondary hyperparathyroidism occurs in patients with, e.g., renal failure, osteomalacia, and intestinal malabsorption syndrome. In both primary and secondary hyperparathyroidism, bone abnormalities, e.g., the loss of bone mass or decreased mineral content, are common and renal damage is possible. Hyperparathyroidism is thus also characterized by abnormal calcium, phosphorus and bone metabolism.

More recently, other roles for vitamin D have come to light. Specific nuclear receptors for 1α,25-dihydroxyvitamin $D_3$ have been found in cells from diverse organs not involved in calcium homeostasis. For example, Miller et al., 52 *Cancer Res.*(1992) 515–520, have demonstrated biologically active, specific receptors for 1α,25-dihydroxyvitamin $D_3$ in the human prostatic carcinoma cell line, LNCaP.

It has been reported that certain vitamin D compounds and analogs are potent inhibitors of malignant cell proliferation and inducers/stimulators of cell differentiation. For example, U.S. Pat. No. 4,391,802 issued to Suda et al. discloses that 1α-hydroxyvitamin D compounds, specifically, 1α,25-dihydroxyvitamin $D_3$ and 1α-hydroxyvitamin $D_3$, possess potent antileukemic activity by virtue of inducing the differentiation of malignant cells (specifically, leukemia cells) to nonmalignant macrophages (monocytes), and are useful in the treatment of leukemia. In another example, Skowronski et al., 136 *Endocrinology* 20–26 (1995), have reported antiproliferative and differentiating actions of 1α,25-dihydroxyvitamin $D_3$ and other vitamin $D_3$ analogs on prostate cancer cell lines.

Previous proliferation studies, such as those cited above, focused exclusively on vitamin $D_3$ compounds. Even though such compounds may, indeed, be highly effective in differentiating malignant cells in culture, their practical use in differentiation therapy as anticancer agents is severely limited because of their equally high potency as agents affecting calcium metabolism. At the levels required in vivo for effective use as antileukemic agents, these same compounds can induce markedly elevated and potentially dangerous blood calcium levels by virtue of their inherent calcemic activity. In other words, the clinical use of 1α,25-dihydroxyvitamin $D_3$ and other vitamin $D_3$ analogs as anticancer agents is precluded, or severely limited, by the risk of hypercalcemia.

Still other roles for vitamin D have been suggested in modulation of the immune response (see, e.g., U.S. Pat. No. 4,749,710 issued to Truitt et al.; U.S. Pat. No. 5,559,107 issued to Gates et al.; U.S. Pat. Nos. 5,540,919; 5,518,725 and 5,562,910 issued to Daynes et al.) and the inflammatory response (see, e.g., U.S. Pat. No. 5,589,471 issued to Hansen et al.).

Considering the diverse biological actions of vitamin D and its potential as a therapeutic agent, a need exists for compounds with greater specific activity and selectivity of action, e.g., vitamin D compounds with antiproliferative and differentiating effects but which have less calcemic activity than therapeutic amounts of the known compounds or analogs of vitamin D.

BRIEF SUMMARY OF THE INVENTION

The present invention provides novel 1α-hydroxyvitamin D compounds represented by general formula (I):

D-Z    (I)

wherein D is a moiety which is $D^1$, $D^2$ or $D^3$ in which $D^1$ is a 1α-hydroxyvitamin D, $D^2$ is a 1α-hydroxyprevitamin D, and $D^3$ is a 1α-hydroxycholesterol or a 1α-hydroxyergosterol moiety described hereinafter as formulas (II), (III) and (IV), respectively, and wherein Z represents a C-17 sidechain which is saturated or unsaturated, substituted or unsubstituted, straight or branched $C_1$–$C_8$ hydrocarbon group in which the C-25 or equivalent position has a double bond. The invention also provides a method for treating or preventing certain diseases and disorders. Such diseases and disorders include (i) hyperparathyroidism by lowering (or maintaining low) serum parathyroid hormone levels; (ii) hyperproliferative diseases; (iii) immune response imbalance; (iv) inflammatory diseases; and (v) bone depletive disorders.

The foregoing, and other advantages of the present invention, are realized in one aspect thereof in a compound of formula (I) described hereinbelow. The compound of formula (I) is a vitamin D compound which is characterized by a double bond at the C-25 position of the C-17 side chain of vitamin D and which has potent biological activity but low calcemic activity relative to the active forms of vitamin $D_3$. Preferably such compounds are 1α-hydroxylated prodrugs which are hydroxylated in vivo at the C-24 position to form 1,24-dihydroxylated compounds.

As used herein, the term "vitamin D compound" is meant to refer to compounds which fall within the generic structure of formula (I) having vitamin D hormonal bioactivity. It is also noted that a shorthand notation is often used for the D hormones, e.g., 1α-hydroxyvitamin $D_2$ may be referred to as simply 1α-OH-$D_2$.

In another aspect, the invention is a pharmaceutical composition which includes, in unit dosage form, an effective amount of a vitamin D compound of formula (I) and a pharmaceutically acceptable excipient.

The treatment methods of the present invention are alternatives to conventional therapies with 1α,25-dihydroxyvitamin $D_3$ or 1α-hydroxyvitamin $D_3$; the methods are characterized by providing the compound of formula (I) having equivalent bioactivity but much lower toxicity than these conventional therapies.

Other advantages and a fuller appreciation of the specific attributes of this invention will be gained upon an examination of the following drawings, detailed description of preferred embodiments, and appended claims. It is expressly understood that the drawings are for the purpose of illustration and description only, and are not intended as a definition of the limits of the invention.

BRIEF DESCRIPTION OF THE DRAWING(S)

The preferred exemplary embodiment of the present invention will hereinafter be described in conjunction with the appended drawing wherein like designations refer to like elements throughout and in which:

FIG. 1 is an exemplary reaction scheme for the preparation of 1α-hydroxy-25-ene-vitamin $D_2$.

DETAILED DESCRIPTION OF THE INVENTION

Figure 1:
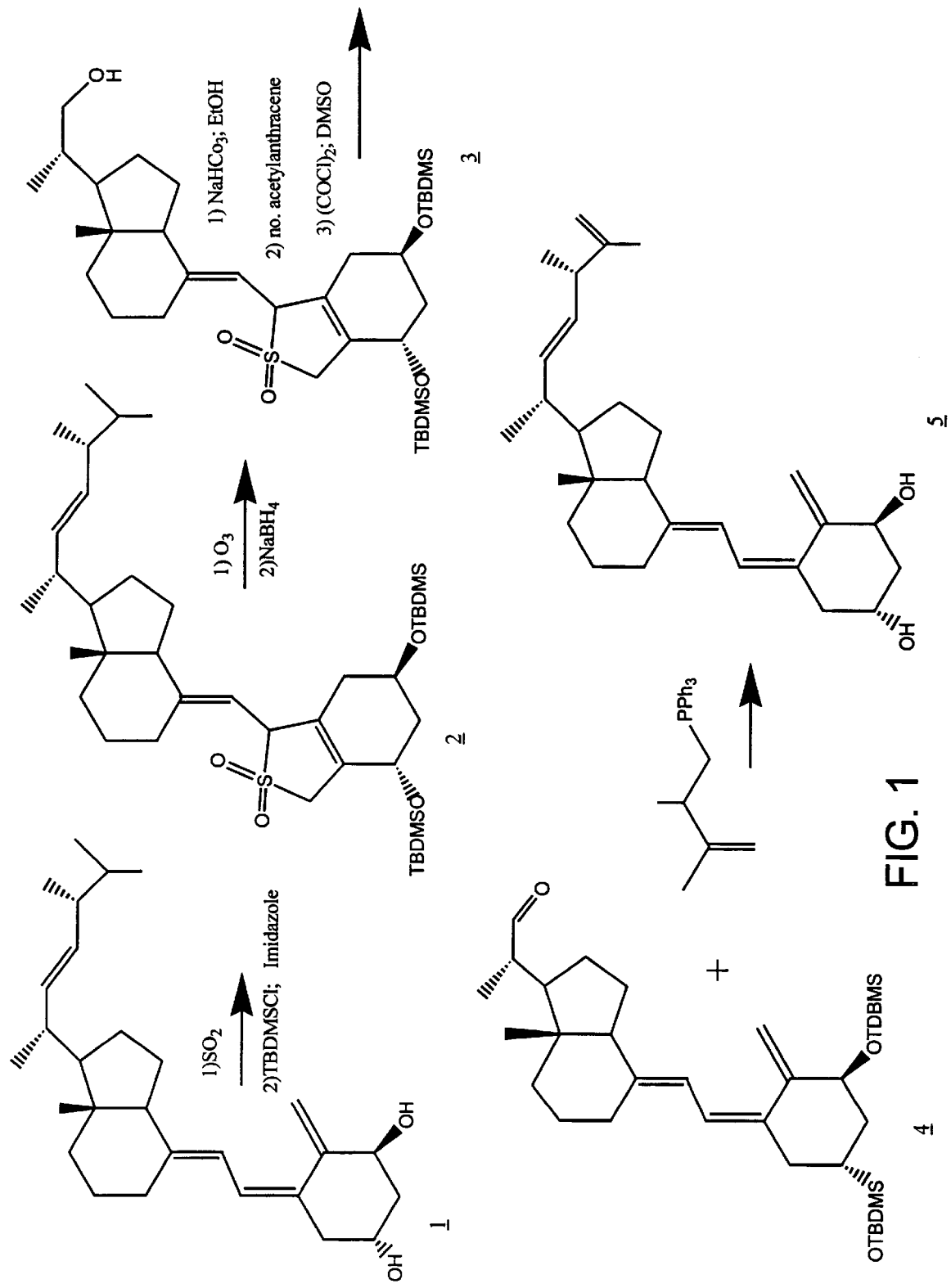

The present invention relates to 1α-hydroxyvitamin D compounds which are 1α-hydroxy-25-ene-vitamin D compounds and analogs thereof. The compounds of the present invention are most particularly adapted for use in the treatment and prophylaxis of certain diseases and disorders, e.g., hyperproliferative diseases, hyperparathyroidism and certain immune response conditions. Such hyperproliferative diseases include skin, breast, colon and prostate cancer and psoriasis. Hyperparathyroid diseases include primary and secondary hyperparathyroidism. Immune response conditions include autoimmune diabetes, multiple sclerosis and transplant rejection. Accordingly, the present invention will now be described in detail with respect to such endeavors; however, those skilled in the art will appreciate that such a description of the invention is meant to be exemplary only and should not be viewed as limitative on the full scope thereof.

The 1α-hydroxy-25-ene-vitamin D compounds and derivatives thereof find value as pharmaceutical agents. These compounds are suitably prodrugs for 1α,24-dihydroxylated vitamin D compounds as they are hydroxylated in vivo at the 24-position to become the active forms of vitamin D. As prodrugs, these compounds in effect circumvent the first pass concern over intestinal vitamin D receptor binding which mediates intestinal calcium absorption, thereby resulting in reduced or no hypercalcemia compared with similar dosing with known active vitamin D compounds such as 1α,25-dihydroxyvitamin $D_3$.

In the following description of the method of the invention, process steps are carried out at room temperature and atmospheric pressure unless otherwise specified.

As used herein, the terms "substantially pure" or "substantially free" refer to a purity of at least 90%. The term "substantially less" refers to at least 25% less than the comparative substance. Also, as used herein, the term "lower" as a modifier for alkyl, alkenyl, fluoroalkyl, fluoroalkenyl or cycloalkyl is meant to refer to a straight or branched, saturated or unsaturated hydrocarbon group having 1 to 4 carbon atoms. Specific examples of such hydrocarbon groups are methyl, ethyl, propyl, isopropyl, butyl, isobutyl, t-butyl, ethenyl, propenyl, butenyl, isobutenyl, isopropenyl, formyl, acetyl, propionyl, butyryl or cyclopropyl. As used herein, the term "hydrocarbon moiety" refers to a lower alkyl, a lower alkenyl or a lower cycloalkyl, i.e., a straight or branched, saturated or unsaturated $C_1$–$C_4$ hydrocarbon group. Also, the term "equivalent position," as in, e.g., C-24 or equivalent position, is meant to refer to a particular carbon in the C-17 side chain of a vitamin D compound wherein that carbon would be the C-24 carbon but for homologation of the side chain.

In one aspect, the present invention provides novel 1α-hydroxylated vitamin D compounds and analogs thereof. The vitamin D compounds operable in the present invention are suitably represented by general formula (I):

D-Z  (I)

wherein D is a moiety which is $D^1$, $D^2$ or $D^3$ in which $D^1$ is a 1α-hydroxyvitamin D, $D^2$ is a 1α-hydroxyprevitamin D and $D^3$ is a 1α-hydroxycholesterol or a 1α-hydroxyergosterol moiety described hereinafter as formulas (II), (III) and (IV), respectively, and wherein Z represents a C-17 sidechain which is a saturated or unsaturated, substituted or unsubstituted, straight-chain or branched $C_4$–$C_8$ hydrocarbon group in which the C-24 or equivalent position is bonded by a single C—C bond to a lower alkyl, lower fluoroalkyl, lower alkenyl or lower fluoroalkenyl group and in which the C-25 or equivalent position has a double bond.

It is noted that previtamin D compounds are the thermal isomers of the corresponding vitamin D compounds, e.g., 1-hydroxyprevitamin $D_2$ is the thermal isomer of 1-hydroxyvitamin $D_2$, and exists in thermal equilibrium with same. Cholesterol and ergosterol compounds are the well-known precursors in the biosynthesis of vitamin D compounds.

Preferably, $D^1$-Z is a 1α-hydroxyvitamin D compound characterized by the general formula (II):

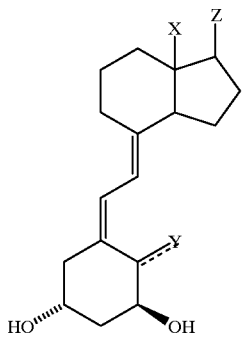

(II)

wherein Z is as described above; Y is a methylene group if the bond to Y is a double bond or a methyl group or hydrogen if the bond to Y is a single bond, i.e., when Y is hydrogen, the compound of formula (II) is a 19-nor compound; and X is hydrogen, lower alkyl or lower fluoroalkyl.

Another example of $D^1$-Z compound is represented by formula (IIA) below:

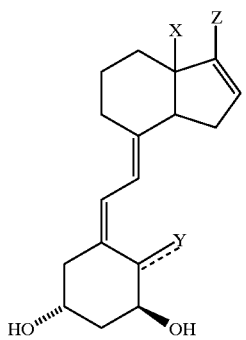

(IIA)

wherein Z, X and Y are as defined above.

$D^2$-Z is a 1α-hydroxyprevitamin D compound represented by the general formula (III):

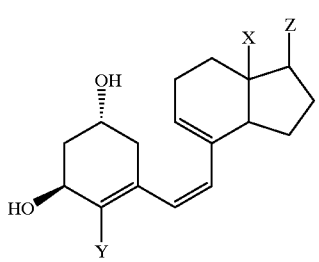

(III)

wherein Z and X are as described above, and Y is hydrogen or a methyl group.

$D^3$-Z is a 1α-hydroxycholesterol or 1α-hydroxyergosterol compound characterized by the general formula (IV):

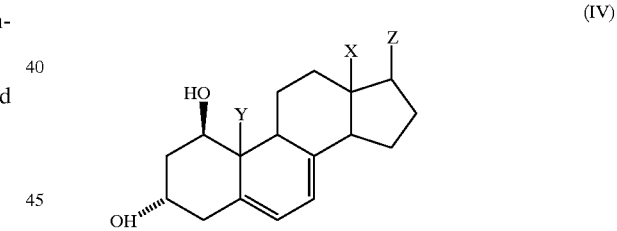

(IV)

wherein Z and X are as described above and Y is hydrogen or a methyl group.

Preferably, Z, the C-17 side chain, is represented by the general formula (VA):

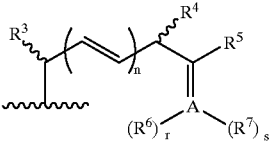

(VA)

wherein n is an integer which is 1 or 2; $R^3$ is hydrogen, lower alkyl, lower fluoroalkyl, lower alkenyl or lower fluoroalkenyl; $R^4$ and $R^5$ are independently lower alkyl, lower fluoroalkyl, lower alkenyl or lower fluoroalkenyl; A is carbon, oxygen, sulfur or nitrogen; r is 1 and s is zero when A is nitrogen; r and s are 1 when A is carbon; r and s are zero when A is sulfur or oxygen; and $R^6$ and $R^7$ are independently hydrogen, lower alkyl, lower alkenyl, lower fluoroalkyl or lower fluoroalkenyl. As to the bond to which n refers, this bond is a —CH$_2$—CH$_2$— or a —CH═CH—group.

For example, Z includes a side chain wherein A is carbon, r and s are 1 and n is 1 and which is represented by formula (VB):

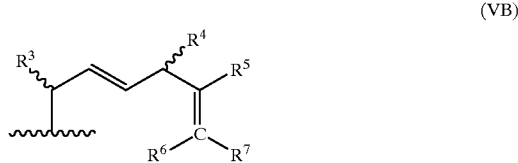

(VB)

wherein $R^3$, $R^6$ and $R^7$ are independently hydrogen, lower alkyl, lower fluoroalkyl, lower alkenyl or lower fluoroalkenyl, and $R^4$ and $R^5$ independently are lower alkyl, lower fluoroalkyl, lower alkenyl or lower fluoroalkenyl.

Also, Z includes a side chain represented by formula (VC):

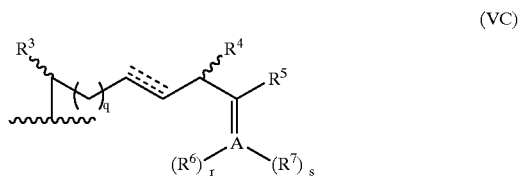

(VC)

wherein a dotted line along the side chain represents an optional additional C—C bond; q is zero or an integer which is 1 or 2; $R^3$ is hydrogen, lower alkyl, lower fluoroalkyl, lower alkenyl or lower fluoroalkenyl; $R^4$ and $R^5$ are independently lower alkyl, lower fluoroalkyl, lower alkenyl or lower fluoroalkenyl; A is carbon, oxygen, sulfur or nitrogen; r is 1 and s is zero when A is nitrogen; r and s are 1 when A is carbon; r and s are zero when A is sulfur or oxygen; $R^6$ and $R^7$ are independently hydrogen, lower alkyl, lower alkenyl, lower fluoroalkyl or lower fluoroalkenyl. As to the optional C—C bonds, for example, if q═0, there may be a single, double or triple bond between C-22 and C-23. As to the group to which q refers, this is a —CH$_2$— group.

For example, Z includes a side chain wherein q is zero, A is carbon, r and s are 1 and which is represented by formula (VD):

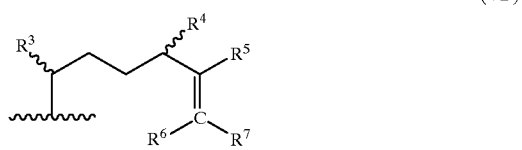

(VD)

wherein $R^3$, $R^6$ and $R^7$ are independently hydrogen, lower alkyl, lower fluoroalkyl, lower alkenyl or lower fluoroalkenyl, and $R^4$ and $R^5$ independently are lower alkyl, lower fluoroalkyl, lower alkenyl or lower fluoroalkenyl.

Preferred among the compounds of formula (I) are the 1α-hydroxy compounds which are prodrugs for 1α,24-dihydroxylated vitamin D. Examples of the compounds of formula (I) are:

1α-hydroxy-25-ene-vitamin D$_2$
1α-hydroxy-25-oxo-vitamin D$_2$
1α-hydroxy-25-ene-vitamin D$_4$
1α-hydroxy-25-oxo-vitamin D$_4$ Preferred among the compounds of formula (III) are the 1-hydroxy previtamin D compounds which are prodrugs and isomers for 1α,24-dihydroxylated vitamin D. Examples of the compounds of formula (III) are:

1α-hydroxy-25-ene-previtamin D$_2$
1α-hydroxy-25-oxo-previtamin D$_2$
1α-hydroxy-25-ene-previtamin D$_4$
1α-hydroxy-25-oxo-previtamin D$_4$ Preferred among the compounds of formula (IV) are the 1-hydroxylated precursor compounds of vitamin D compounds, i.e., 1-hydroxylated cholesterol or ergosterol compounds, which are also prodrugs for 1α,24-dihydroxylated vitamin D. Examples of the compounds of formula (IV) are:

1α-hydroxy-24-methyl-25-ene-cholesterol
1α-hydroxy-25-ene-ergosterol
1α-hydroxy-24-methyl-25-oxo-cholesterol
1α-hydroxy-25-oxo-ergosterol Among those compounds of the present invention that have chiral centers, e.g., in the C-17 sidechain at C-20 or C-24, it is understood that both diastereomers (e.g., R and S) and the mixture thereof are within the scope of the present invention.

The compounds of formula (I) when administered in vivo are hydroxylated at C-24. For example, a 1α,24-hydroxylated compound in accordance with the present invention has a Z side chain represented by formula (VE):

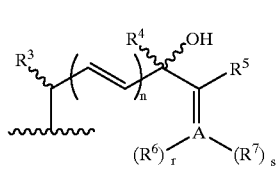

(VE)

or formula (VF):

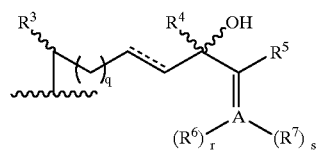

(VF)

wherein all dotted lines, n, q, A and R groups are as defined above. Further, a specific stereoisomer configuration at the C-24 or equivalent position may be suitably represented by formula (VG):

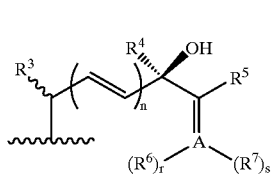

(VG)

or by formula (VH):

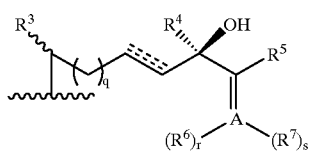

wherein all dotted lines, n, q, A and R groups are as defined above.

The compounds of formula (I) may be prepared by the exemplary reaction process depicted in FIG. 1. The synthesis is characterized by coupling the appropriate and separately synthesized side chain unit to the desired preformed vitamin D nucleus bearing a displacable group at C-22. The required side chain is prepared as a phenylphosphine derivative, i.e., a Wittig reagent (e.g., see, White et al., 1 *J. Chem. Soc. Perkin Trans.* (1993) 759; Nishigaichi et al. *Chem. Lett.* (1996) 961., both of which are incorporated herein by reference).

Specifically, the method of the present invention for preparing the 1α-hydroxylated compounds entails using 1α-hydroxyvitamin $D_2$ as a starting material and forming 1α-hydroxy-25-ene-vitamin $D_2$.

As seen in FIG. 1, 1α-hydroxyvitamin $D_2$ (1) is reacted with $SO_2$ and the hydroxyl functionalities at the C-3 and C-1 positions are protected with t-butyldimethylsilylchloride in the presence of imidazole, affording the adduct intermediate (2). Ozonolysis and reduction affords a C-22 alcohol (3) (see, Manchand et al., 60 *J. Org. Chem.* (1995) 6574, incorporated herein by reference). $SO_2$ extrusion ($NaHCO_3$; EtOH), isomerization (no. acetylanthracene) and subsequent oxidation using the known Swern oxidation (($COCl)_2$; DMSO) affords the C-22 aldehyde (4). The side chain is introduced by reaction of aldehyde (4) with Wittig reagent and appropriate deprotection by known methods to yield the 1α-hydroxy-25-ene-vitamin $D_2$ compound (5).

The compounds of formula (III) may be generally prepared by the process of FIG. 1 wherein the previtamin starting materials can be prepared by the exemplary reaction processes given in, e.g., U.S. Pat. No. 5,252,191 issued to Pauli et al.; U.S. Pat. No. 5,035,783 issued to Goethals et al; U.S. Pat. No. 4,388,243, all of which are incorporated herein by reference. The 19-nor compounds of formula (I) may be prepared generally by the exemplary reaction process given herein, the starting material for which may be prepared by the process given in U.S. Pat. No. 5,710,294 incorporated herein by reference. The process given in FIG. 1 is also suitable for preparation of compounds of formula (IV) wherein the cholesterol or ergosterol starting materials are commercially available.

The compounds of the present invention are useful as active compounds in pharmaceutical compositions having reduced side effects and low toxicity as compared with the well-known active forms of vitamin $D_3$, 1α,25-dihydroxyvitamin $D_3$ and 1α-hydroxyvitamin $D_3$. The compounds are especially of value for both local, including topical, and systemic treatment and prophylaxis of human and veterinary disorders which are characterized by (i) abnormal cell proliferation and/or cell differentiation, e.g., cancers such as skin, breast, colon and prostate and dermatological disorders such as psoriasis; (ii) imbalance of the immune system, e.g., autoimmune diseases such as multiple sclerosis and diabetes, and rejection of transplants; (iii) abnormal interleukin-1 production, e.g., inflammatory response disorders such as rheumatoid arthritis and asthma; (iv) abnormal parathyroid hormone production, e.g., hyperparathyroidism, both primary and secondary; and (v) loss of bone mass or bone mineral content.

The 1-hydroxyvitamin D compounds of the present invention are those that have a lower tendency or inability to cause the undesired side effects of hypercalcemia and/or hypercalciuria. In other words, the compounds of the present invention can be administered at dosages that allow them to act, e.g., as antiproliferative agents and cell differentiation agents when exposed to malignant or other hyperproliferative cells without significantly altering calcium metabolism. This selectivity and specificity of action makes the 1-hydroxyvitamin D compounds of the present invention useful and preferred agents for, e.g., safely inhibiting hyperproliferation and promoting malignant or hyperplastic cell differentiation. The 1-hydroxyvitamin D compounds of the present invention, thus, overcome the shortcomings of the known active vitamin $D_3$ compounds described above, and can be considered preferred agents for the control and treatment of malignant diseases such as prostate cancer as well as benign prostatic hyperplasia, skin diseases, such as skin cancer and psoriasis, breast cancer and colon cancer, immune and inflammatory response disorders, and hyperparathyroidism. For example, as to the latter, the analogs of formula (I) are substantially less toxic than their vitamin $D_3$ counterparts when administered to patients experiencing hyperparathyroidism. For patients using oral calcium phosphate binders, administration of the analogs of formula (II) at dosage levels higher than possible with the vitamin $D_3$ compounds may provide greater efficacy than heretofore possible in treating hyperparathyroidism.

The pharmacologically active compounds of this invention are suitably processed in accordance with conventional methods of pharmacy to produce medicinal compositions for administration to patients, e.g., mammals including humans, in, e.g., admixtures with conventional excipients such as pharmaceutically acceptable organic or inorganic carrier substances which do not deleteriously react with the active compounds, and optionally, other therapeutic ingredients. Any suitable route of administration may be employed for providing an effective dosage of the compounds in accordance with the present invention. For example, oral, rectal, topical, parenteral, intravenous, intramuscular, subcutaneous, ocular, nasal, buccal, and the like routes may be employed.

Therapeutic and prophylactic compositions are those suitable for the various routes of administration described herein, although the most suitable route in any given case will depend on the nature and severity of the condition being treated and on the nature of the active ingredient. They are conveniently presented in unit dosage form.

Suitable pharmaceutically acceptable carriers for use in the composition and method of the present invention include, but are not limited to water, salt solutions (e.g., buffer solutions), alcohols including benzyl alcohols, gum arabic, mineral and vegetable oils (e.g., corn oil, cottonseed oil, peanut oil, olive oil, coconut oil), fish liver oils, oily esters such as Polysorbate 80, polyethylene and propylene glycols, gelatin, carbohydrates (e.g., lactose, amylose or starch), magnesium stearate, talc, silicic acid, viscous paraffin, fatty acid monoglycerides and diglycerides, pentaerythritol fatty acid esters, hydroxymethylcellulose, polyvinyl pyrrolidone, etc.

The pharmaceutical preparations can be sterilized and, if desired, be mixed with auxiliary agents, e.g., lubricants, preservatives, stabilizers, wetting agents, emulsifiers, salts for influencing osmotic pressure, buffers, coloring and flavoring. If a solid carrier is used, the dosage form of the compounds of the present invention may be tablets, capsules, powders, suppositories, or lozenges. If a liquid carrier is used, soft gelatin capsules, transdermal patches, aerosol sprays, topical creams, syrups or liquid suspensions, emulsions or solutions may be the dosage form.

It is noted, however, that dosage forms of 1-hydroxyprevitamin D are most suitably formulated with carriers such as starch, lactose or amylose, which do not deleteriously react with the active compounds. The formulations can be produced in tablet, capsule, powder and lozenge form. However, whatever method of formulation is used, care should be taken to avoid exposure to solvents and heat as, under such conditions, there is a tendency for 1-hydroxyprevitamin D to convert to 1-hydroxyvitamin D, i.e., the compounds of formula (III) are preferably formulated in solvent-free, crystalline, heat-stable form. Because heat and solvents are to be avoided, the preferred method of tablet formulation is dry granulation.

For parenteral application, particularly suitable are injectable, sterile solutions, preferably oily or aqueous solutions, as well as suspensions, emulsions, or implants, including suppositories. Ampules are convenient unit dosages. The dosage of the analogs in accordance with the present invention for parenteral administration generally is about 1–30 $\mu$g given 1 to 3 times per week.

As noted above, for enteral application, particularly suitable are tablets, dragées, liquids, drops, suppositories, or capsules. A syrup, elixir, or the like can be used wherein a sweetened vehicle is employed.

For rectal administration, compounds are formed into a pharmaceutical composition containing a suppository base such as cacao oil or other triglycerides. To prolong storage life, the composition advantageously includes an antioxidant, such as ascorbic acid, butylated hydroxyanisole or hydroquinone.

For topical application, there are also employed as non-sprayable forms, viscous to semi-solid or solid forms comprising a carrier compatible with topical application and having a dynamic viscosity preferably greater than water. Suitable topical formulations include transdermal devices, solutions, suspensions, emulsions, aerosols, creams, ointments, liniments, salves, lotions, dusting powders and the like which are, if desired, sterilized or mixed with auxiliary agents, e.g., preservatives, etc.

The magnitude of a prophylactic or therapeutic dose of the compounds in accordance with the present invention will vary with the nature or the severity of the condition to be treated and with the particular composition and its route of administration. Oral administration of the pharmaceutical compositions of the present invention is preferred.

In general, the daily dosage of the compounds according to this invention generally is about 0.025 to about 7.5 nmol/kg of body weight of the patient, preferably about 0.025 to about 1 nmol/kg. Generally, the compounds of this invention are dispensed by unit dosage form in a pharmaceutically acceptable carrier. Generally, the compounds of the present invention are dispensed by unit dosage form comprising about 0.25 to about 50.0 $\mu$g in a pharmaceutically acceptable carrier per unit dosage. The dosage of the compounds according to the present invention generally is about 3.5 $\mu$g to about 1000 $\mu$g/week, preferably about 10 $\mu$g to about 500 $\mu$g/week.

For treatment of hyperproliferative diseases such as cancers and psoriasis, the enteral dosage of the compounds of the present invention is about 1 nmol to about 100 nmol per unit dosage; for hyperparathyroidism, about 0.5 nmol to 50 nmol per unit dosage; for treatment of inflammatory diseases, about 1 nmol to 150 nmol per unit dosage; for immune response modulation, about 1 nmol to 150 nmol per unit dosage. Thus, the effective dosage amount on a daily basis per kilogram of body weight of the patient ranges from about 0.01 $\mu$g/kg/day to about 3.0 $\mu$g/kg/day.

In addition, those skilled in the art will also appreciate that such dosages may be encapsulated in time release, e.g., sustained, delayed or directed release delivery systems such as a liposome delivery system, polysaccharides exhibiting a slow release mechanism, salistic or other polymer implants or microspheres, as well as those where the active ingredient is suitably protected with one or more differentially degradable coatings, e.g., by microencapsulation, enteric coating, multiple coatings, etc., and such means effect continual dosing of compositions contained therein. For example, an enteric coating is suitably one which is resistant to disintegration in gastric juice. It is also possible to freeze-dry the active ingredient and use the lyophilizate obtained, e.g., for the preparation of products for injection.

It will be appreciated that the actual preferred amounts of active analog in a specific case will vary according to the specific compound being utilized, the particular compositions formulated, the mode of application, and the particular sites being treated. Dosages can be determined using conventional considerations, e.g., by customary comparison of the differential activities of the subject compounds and of a known agent, e.g., by means of an appropriate conventional pharmacological protocol.

The specific doses for each particular patient depend on a wide variety of factors, for example, on the efficacy of the specific compound employed, on the age, body weight, general state of health, sex of patient, on the diet, on the timing and mode of administration, on the rate of excretion, and on medicaments used in combination and the severity of the particular disorder to which the therapy is applied.

As described hereinbefore, the compounds of the present invention are preferably administered to the human (or veterinary) patients in oral dosage formulation. As a compound in accordance with the present invention is released from the oral dosage formulation, it is absorbed from the intestine into the blood. The compounds of the present invention then undergo hydroxylation at the 1$\alpha$-position of the D-ring of the vitamin ring structure, thus providing an active form of the vitamin D compound which is 1$\alpha$,24-dihydroxylated. As to the compounds of formula (I), little or no first pass interaction with the intestinal vitamin D receptors is to be expected, thus, yielding little or no stimulation of intestinal calcium absorption. In the case of the 1-hydroxyprevitamin D compounds of formula (III), as these compounds are warmed by the core temperature of the animal or human, they convert to the corresponding 1-hydroxyvitamin D which are then 24-hydroxylated to form the 1,24-dihydroxy compounds. It is noted that 1$\alpha$-hydroxyprevitamin D compounds before thermal and metabolic activation do not interact with the intestinal vitamin D receptors and, thus, do not stimulate first-pass intestinal calcium absorption.

The dosage forms may also contain adjuvants as well as other therapeutically valuable substances or may contain more than one of the compounds specified herein in admixture.

Thus, a further aspect within the scope of the present invention is administration of effective dosages of the compounds of the present invention in conjunction with administration of other hormones or other agents which have been shown to have efficacy in the treatment and present of the diseases and disorders described herein.

For example, compounds of the present invention are suitably co-administered with agents known to ameliorate bone diseases or disorders. Such bone agents may include conjugated estrogens or their equivalents, antiestrogens, calcitonin, bisphosphonates, calcium supplements, calcium receptor agonists, cobalamin, pertussis toxin, boron, dehydroepiandrosterone (DHEA) and other bone growth factors such as transforming growth factor beta, activin or bone morphogenic protein. Possible dose ranges for certain of these co-administered agents are provided in Table 1.

TABLE 1

Possible Oral Dose Ranges for Various Agents
Co-Administered With 1α-Hydroxyvitamin $D_2$

| | Dose Ranges | | |
|---|---|---|---|
| Agent | Broad | Preferred | Most Preferred |
| Conjugated Estrogens or Equivalent (mg/day) | 0.3–5.0 | 0.4–2.4 | 0.6–1.2 |
| Sodium Fluoride (mg/day) | 5–150 | 30–75 | 40–60 |
| Calcitonin (IU/day) | 5–800 | 25–500 | 50–200 |
| Calcium Receptor Agonists (mg/day) | 4–1000 | 20–800 | 50–60 |
| Bisphosphonates (μg/day) | 50–20,000 | 100–15,000 | 250–10,000 |
| Calcium Supplements (mg/day) | 250–2500 | 500–1500 | 750–1000 |
| Cobalamin (μg/day) | 5–200 | 20–100 | 30–50 |
| Pertussis Toxin (mg/day) | 0.1–2000 | 10–1500 | 100–1000 |
| Boron (mg/day) | 0.10–3000 | 1–250 | 2–100 |

Antiestrogens, such as Tamoxifen™, are also known bone agents as well as antiproliferative agents and may be suitably used in conjunction with the 1α-hydroxyvitamin D and 1α-hydroxyprevitamin D compounds of the present invention.

Although the above examples detail dosage by mouth, it is to be understood that the combinations of agents can also be administered in alternative fashions, including intranasally, transdermally, intrarectally, intravaginally, subcutaneously, intravenously, and intramuscularly.

Also provided herein are compounds of the present invention which are co-administered with known cytotoxic agents. Such agents include estramustine phosphate, prednimustine, cisplatin, 5-fluoro-uracil, melphalan, hydroxyurea, mitomycin, idarubicin, methotrexate, adriamycin and daunomycin. It is anticipated that a 1α-hydroxyvitamin D of the present invention used in combination with various anticancer drugs can give rise to a significantly enhanced cytotoxic effect on cancerous cells, thus providing an increased therapeutic effect. Specifically, as a significantly increased growth-inhibitory effect is obtained with the above-disclosed combinations utilizing lower concentrations of the anticancer drugs compared to the treatment regimens in which the drugs are used alone, there is the potential to provide therapy wherein adverse side effects associated with the anticancer drugs are considerably reduced than normally observed with the anticancer drugs used alone in larger doses. Possible dose ranges of these co-administered second anticancer agents are about 0.1 μg to 1 μg/kg/day.

The compounds in accordance with the present invention are also suitably co-administered with known antiinflammatory agents. Such agents include both steroidal (e.g., corticosteroids) and nonsteroidal antiinflammatory agents (e.g., salicylates, naproxen). It is anticipated that a compound of the present invention used in combination with these various anti-inflammatory drugs can give rise to a significantly enhanced anti-inflammatory activity, thus providing an increased therapeutic effect.

Also included with the scope of the present invention is the co-administration of compounds in accordance with the present invention with known immune response augmenting agents. Such agents include the cyclosporins, DHEA and DHEA derivatives such as DHEA-sulfate, 16α-bromo-DHEA, 7-oxo-DHEA, 16α-bromo-DHEA-sulfate and 7-oxo-DHEA-sulfate. It is also anticipated that a compound of the present invention used in combination with these various immune response augmenting drugs can give rise to a significantly enhanced immunomodulating activity, thus providing an increased therapeutic effect.

The present invention is further explained by the following examples which should not be construed by way of limiting the scope of the present invention.

EXAMPLE 1

In Vivo Generation of 1α,24(S)—$(OH)_2$-25-ene-$D_2$ from 1α-OH-25-ene-$D_2$

1α-OH-25-ene-$D_2$ is administered (either oral or intraperitoneal supplementation) to vitamin D-replete rats. Lipid extracts of the plasma are prepared and the metabolites purified using the method of Strugnell et al., *Biochem. J.*, 310: 233–241 (1995) (incorporated herein by reference) described below for synthesizing standard biological 1α,24-dihydroxylated vitamin $D_2$ compounds.

Standard biological 1α,24-$(OH)_2$-25-ene-$D_2$ is synthesized in vitro from 1α-OH-25-ene-$D_2$ by incubating 10 μg of 1α-OH-25-ene-$D_2$ in a flask containing 5 mL of 20% liver homogenates made from vitamin D-deficient chicks. The product of this reaction is isolated by HPLC and identified by mass spectrometry. In the lipid extracts of the plasma from the vitamin D-replete rats administered 1α-OH-25-ene-$D_2$, one metabolite isolated is found to co-migrate on HPLC with the standard 1α,24-$(OH)_2$-25-ene-$D_2$.

EXAMPLE 2

In Vivo Generation of 1α,24(S)—$(OH)_2$-25-ene-$D_2$ from 1α-OH-25-ene-pre$D_2$

Male weanling rats are fed a diet replete in vitamin D and with normal calcium (0.47%). After a period of four weeks has elapsed, the rats are divided into two groups, and orally administered either 1α-OH-25-ene-pre$D_2$ (0.25 μg/kg) in a vehicle such as lactose or the vehicle (control) alone. Four hours after administration, the rats are killed and their blood level of 1α,24(S)—$(OH)_2$-25-ene-$D_2$ is measured using a standard technique.

Following this procedure demonstrates that the 1α,24 (S)—$(OH)_2$-25-ene-$D_2$ level is significantly elevated.

EXAMPLE 3

Production of 1α,24(S)—$(OH)_2$-25-ene-$D_2$ in Osteoporotic Women Administered 1α-(OH)-25-ene-$D_2$ Human female subjects, who have been diagnosed with osteoporosis, are given daily doses of 25 μg/day 1α-OH-25-ene-$D_2$ for one week. Blood is collected and analyzed for the metabolite 1α,24(S)—$(OH)_2$-25-ene-$D_2$. Lipid is extracted from the blood, and the metabolite is purified by HPLC using standard methods and quantified with the radioreceptor assay produced by Incstar (Stillwater, Minn.). One day following the last dose of 25 μg, the results show that there is a significant level of 1α,24(S)—$(OH)_2$-25-ene-$D_2$ in the blood.

EXAMPLE 4
Treatment of Osteoporosis with $1\alpha$-OH-25-ene-preD$_2$

A clinical study is conducted with postmenopausal osteoporotic outpatients having ages between 55 and 75 years. The study involves up to 120 patients randomly divided into three treatment groups, and continues for 24 months. Two of the treatment groups receive constant dosages of orally administered $1\alpha$-OH-25-ene-preD$_2$ (u.i.d.; two different dose levels above 5.0 μg/day) and the other group receives a matching placebo. All patients maintain a normal intake of dietary calcium (500 to 800 mg/day) and refrain from using calcium supplements. Efficacy is evaluated by pretreatment and posttreatment comparisons of the patient groups with regard to (a) total body, radial, femoral, and/or spinal bone mineral density as determined by x-ray absorptiometry (DEXA), (b) bone biopsies of the iliac crest, and (c) determinations of serum osteocalcin. Safety is evaluated by comparisons of urinary hydroxyproline excretion, serum and urine calcium levels, creatinine clearance, blood urea nitrogen, and other routine determinations.

This study demonstrates that patients treated with orally administered $1\alpha$-OH-25-ene-preD$_2$ exhibit significantly higher total body, radial, femoral, and/or spinal bone densities relative to patients treated with placebo. The treated patients also exhibit significant elevations in serum osteocalcin. Bone biopsies from the treated patients show that $1\alpha$-OH-25-ene-preD$_2$ stimulates normal bone formation. The monitored safety parameters confirm an insignificant incidence of hypercalcemia or hypercalciuria, or any other metabolic disturbance with $1\alpha$-OH-25-ene-preD$_2$.

EXAMPLE 5
Preventive Treatment of Bone Mass Loss in Postmenopausal Osteoporotic Women with $1\alpha$-OH-25-ene-D$_2$ A clinical study is conducted with postmenopausal osteoporotic out-patients having ages between 55 and 75 years. The study involves up to 120 patients randomly divided into three treatment groups and continues for 24 to 36 months. Two of the treatment groups receive constant dosages of $1\alpha$-OH-25-ene-D$_2$ (u.i.d.; two different dose levels at or above 5.0 μg/day) and the other group receives a matching placebo. All patients maintain a normal intake of dietary calcium (500 to 800 mg/day) and refrain from using calcium supplements. Efficacy is evaluated by pre-and posttreatment comparisons of the patient groups with regard to (a) total body calcium retention, and (b) radial and spinal bone mineral density as determined by dual-photon absorptiometry (DPA) or dual-energy x-ray absorptiometry (DEXA). Safety is evaluated by comparisons of urinary hydroxyproline excretion, serum and urine calcium levels, creatinine clearance, blood urea nitrogen, and other routine determinations.

The results show that patients treated with $1\alpha$-OH-25-ene-D$_2$ exhibit significantly higher total body calcium, and radial and spinal bone densities relative to patients treated with placebo. The monitored safety parameters confirm an insignificant incidence of hypercalcemia or hypercalciuria, or any other metabolic disturbance with $1\alpha$-OH-25-ene-D$_2$ therapy.

EXAMPLE 6
Treatment of Psoriasis with $1\alpha$-OH-25-ene-D$_2$

An oral dosage formulation containing $1\alpha$-OH-25-ene-D$_2$ is evaluated in a double blind study for therapeutic efficacy of the formulation in the treatment of dermatitis (contact and ectopic). The formulation evaluated contains 100 to 200 μg of $1\alpha$-OH-25-ene-D$_2$. The control formulation is identical except that it does not contain the $1\alpha$-OH-25-ene-D$_2$. The patients are treated in an outpatient clinic and are divided into an experimental and control population. They are instructed to take the medication once a day, in the morning before breakfast.

In each patient (experimental and control) an area of the skin containing a lesion is selected which is ordinarily covered by clothing, and the patients are instructed not to expose the skin area selected for study to sunlight. The area of the lesion is estimated and recorded, and the lesion(s) is photographed. Relevant details of the photographic procedure are recorded so as to be reproduced when the lesions are next photographed (distance, aperture, angle, background, etc.).

Evaluations of erythema, scaling, and thickness are conducted at weekly intervals by a physician. The final evaluation is usually carried out at the end of four to six weeks of treatment. The results of the study show that daily oral administration of $1\alpha$-OH-25-ene-D$_2$ significantly reduces the degree of erythema, scaling, and thickness versus the control patients.

EXAMPLE 7
Treatment of Psoriasis with $1\alpha$-OH-25-ene-preD$_2$

An oral dosage formulation containing $1\alpha$-OH-25-ene-preD$_2$ is evaluated in a double blind study for therapeutic efficacy of the formulation in the treatment of dermatitis (contact and ectopic). The formulation evaluated contains 10.0 to 20.0 μg of $1\alpha$-OH-25-ene-preD$_2$. The control formulation is identical except that it does not contain the $1\alpha$-OH-25-ene-preD$_2$. The patients are treated in an outpatient clinic and are divided into an experimental and control population. They are instructed to take the medication once a day, in the morning before breakfast.

In each patient (experimental and control) an area of the skin containing a lesion is selected which is ordinarily covered by clothing, and the patients are instructed not to expose the skin area selected for study to sunlight. The area of the lesion is estimated and recorded, and the lesion(s) is photographed. Relevant details of the photographic procedure are recorded so as to be reproduced when the lesions are next photographed (distance, aperture, angle, background, etc.).

Evaluations of erythema, scaling, and thickness are conducted at weekly intervals by a physician. The final evaluation is usually carried out at the end of four to six weeks of treatment. The results of the study show that daily oral administration of $1\alpha$-OH-25-ene-preD$_2$ significantly reduces the degree of erythema, scaling, and thickness versus the control patients.

EXAMPLE 8
Treatment of Prostate Cancer Using $1\alpha$-OH-25-ene-D$_2$

Patients with advanced androgen-independent prostate cancer participate in an open-label study of $1\alpha$-OH-25-ene-D$_2$. Qualified patients are at least 40 years old, exhibit histologic evidence of adenocarcinoma of the prostate, and present with progressive disease which had previously responded to hormonal intervention(s). On admission to the study, patients begin a course of therapy with oral $1\alpha$-OH-25-ene-D$_2$ lasting 26 weeks, while discontinuing any previous use of calcium supplements, vitamin D supplements, and vitamin D hormone replacement therapies. During treatment, the patients are monitored at regular intervals for: (1) hypercalcemia, hyperphosphatemia, hypercalciuria, hyperphosphaturia and other toxicity; (2) evidence of changes in the progression of metastatic disease; and (3) compliance with the prescribed test drug dosage.

The study is conducted in two phases. During the first phase, the maximal tolerated dosage (MTD) of daily oral $1\alpha$-OH-25-ene-D$_2$ is determined by administering progressively higher dosages to successive groups of patients. All doses are administered in the morning before breakfast. The first group of patients is treated with 25.0 μg of $1\alpha$-OH-25-ene-D$_2$. Subsequent groups of patients are treated with 50.0, 75.0 and 100.0 μg/day. Dosing is continued uninterrupted for the duration of the study unless serum calcium exceeds 11.6 mg/dL, or other toxicity of grade 3 or 4 is observed, in which case dosing is held in abeyance until resolution of the observed toxic effect(s) and then resumed at a level which has been decreased by 10.0 μg.

Results from the first phase of the study show that the MTD for 1α-OH-25-ene-$D_2$ is above 25.0 μg/day, a level which is 10- to 50-fold higher than can be achieved with 1α,25-$(OH)_2$-$D_3$. Analysis of blood samples collected at regular intervals from the participating patients reveal that the levels of circulating 1,24(S)—$(OH)_2$-25-ene-$D_2$ increase proportionately with the dosage administered, rising to maximum levels well above 100 pg/mL at the highest dosages, and that circulating levels of 1α,25-$(OH)_2$-$D_3$ are suppressed, often to undetectable levels. Serum and urine calcium are elevated in a dose responsive manner. Patients treated with the MTD of 1α-OH-25-ene-$D_2$ for at least six months report that bone pain associated with metastatic disease is significantly diminished.

During the second phase, patients are treated with 1α-OH-25-ene-$D_2$ for 24 months at 0.5 and 1.0 times the MTD. After one and two years of treatment, CAT scans, X-rays and bone scans used for evaluating the progression of metastatic disease show stable disease or partial remission in many patients treated at the lower dosage, and stable disease and partial or complete remission in many patients treated at the higher dosage.

EXAMPLE 9
Treatment of Prostate Cancer Using 1α-OH-25-ene-pre$D_2$

The study of Example 8 is repeated for the vitamin D compound, 1α-OH-25-ene-pre$D_2$. The results of the phase one study indicate that patients treated with the MTD of 1α-OH-25-ene-pre$D_2$ for at least six months report that bone pain associated with metastatic disease is significantly diminished. The results of the phase two study indicate that after two years, CAT scans, X-rays and bone scans used for evaluating the progression of metastatic disease show stable disease or partial remission in many patients treated at the lower dosage, and stable disease and partial or complete remission in many patients treated at the higher dosage.

EXAMPLE 10
Treatment of Elderly Subjects with Elevated Blood PTH from Secondary Hyperparathyroidism with 1α-OH-25-ene-$D_4$ A twelve-month double-blind placebo-controlled clinical trial is conducted with forty subjects with secondary hyperparathyroidism. The selected subjects have ages between 60 and 100 years and have a history of secondary hyperparathyroidism. Subjects also have femoral neck osteopenia (femoral neck bone mineral density of $\leq 0.70$ g/cm$^2$).

All subjects enter a six-week control period after which the subjects are randomized into two treatment groups: one group receives a constant dosage of 15 μg/day 1α-OH-25-ene-$D_4$, and the other group receives a matching placebo. Both groups maintain a normal intake of dietary calcium without the use of calcium supplements. Efficacy is evaluated by pre- and post-treatment comparisons of the two patient groups with regard to (a) intact PTH (iPTH); (b) radial, femoral and spinal bone mineral density; and (c) bone-specific urine markers (e.g., pyridinium crosslinks). Safety is evaluated by (a) serium calcium and phosphorus, and (b) urine calcium and phosphorus.

Analysis of the clinical data show that 1α-OH-25-ene-$D_4$ significantly decreases iPTH and bone specific urine markers. Subjects treated with this compound show normal serum calcium levels and stable radial and spinal bone densities relative to baseline values. In contrast, patients treated with placebo show no reduction in iPTH and bone-specific urine markers. An insignificant incidence of hypercalcemia is observed in the treatment group.

EXAMPLE 11
Treatment of Elderly Subjects with Elevated Blood PTH from Secondary Hyperparathyroidism with 1α-OH-25-ene-pre$D_2$ A twelve-month double-blind placebo-controlled clinical trial is conducted with forty subjects with secondary hyperparathyroidism. The selected subjects have ages between 60 and 100 years and have a history of secondary hyperparathyroidism. Subjects also have femoral neck osteopenia (femoral neck bone mineral density of $\leq 0.70$ g/cm$^2$).

All subjects enter a six-week control period after which the subjects are randomized into two treatment groups: one group receives a constant dosage of 15 μg/day 1α-OH-25-ene-pre$D_2$, and the other group receives a matching placebo. Both groups maintain a normal intake of dietary calcium without the use of calcium supplements. Efficacy is evaluated by pre- and post-treatment comparisons of the two patient groups with regard to (a) intact PTH (iPTH); (b) radial, femoral and spinal bone mineral density; and (c) bone-specific urine markers (e.g., pyridinium crosslinks). Safety is evaluated by (a) serium calcium and phosphorus, and (b) urine calcium and phosphorus.

Analysis of the clinical data show that 1α-OH-25-ene-pre$D_2$ significantly decreases iPTH and bone specific urine markers. Subjects treated with this compound show normal serum calcium levels and stable radial and spinal bone densities relative to baseline values. In contrast, patients treated with placebo show no reduction in iPTH and bone-specific urine markers. An insignificant incidence of hypercalcemia is observed in the treatment group.

EXAMPLE 12
Treatment of Patients with Secondary Hyperparathyroidism in End Stage Renal Disease with 1α-OH-25-ene-$D_2$ Thirty renal patients are enrolled in a clinical trial to study secondary hyperparathyroidism. The patients show baseline iPTH levels greater than 1000 pg/mL. These greatly elevated levels indicate a component of the disease as primary to the gland as well as a component secondary to the loss of renal function. An initial dose of 1α-OH-25-ene-$D_2$ (50 μg 3 times/week) is increased (maximum, 100 μg 3 times/week) or decreased as necessary to attain and maintain iPTH in the range of 150–300 μg/mL. After 11–12 weeks of treatment, the iPTH levels of the patients decrease to below 1000 pg/mL, and in many cases to below 500 pg/mL. There are few episodes of hypercalcemia with the patients during the study.

EXAMPLE 13
Treatment of Primary Hyperparathyroidism with 1α-OH-25-ene-pre$D_2$ Twenty renal patients are enrolled in a clinical trial to study primary hyperparathyroidism. The patients show baseline iPTH levels greater than 200 pg/mL. An initial dose of 1α-OH-25-ene-pre$D_2$(2–4 μg/day) is increased (maximum, 10 μg/day) or decreased as necessary to attain and maintain iPTH in the normal range. After 11–12 weeks of treatment, the iPTH levels of the patients decrease to below 100 pg/mL, and in many cases to below 50 pg/mL. There are few episodes of hypercalcemia with the patients during the study.

EXAMPLE 14
Immunological Testing of 1α-OH-25-ene-$D_2$

Female C57BL/6 mice are used between the ages of 9–12 weeks. Mice are given food and water ad libitum and are kept in a 12-hour light and 12-hour dark cycle.

A known balanced salt solution (BSS) is prepared and supplemented to 0.01 molar with HEPES buffer.

The test compound, 1α-OH-25-ene-$D_2$, is dissolved in dimethylsulfoxide at final concentrations of 0.2 or 0.4 mg per ml. When working with vitamin D compounds, conditions of reduced lighting are employed.

Mice are apportioned at 4 per group and are inoculated intraperitoneally with $3 \times 10^6$ allogeneic P815 tumor cells and the resulting cytotoxic thymus-derived lymphocyte (CTL) activity is assessed 10 days later. Mice are treated by the intraperitoneal route with 25 microliters of test compound dissolved in dimethylsulfoxide or with dimethylsulfoxide only (vehicle control). In test 1, mice are given daily treatments of 5 micrograms of 1α-OH-25-ene-$D_2$ per day starting one day before immunization and continuing until the day before assay. In test 2, mice are treated with 10 micrograms of 1α-OH-25-ene-$D_2$ only twice: on the day before immunization and on the day of immunization.

Ten days after immunization of mice with P815 cells, single spleen cell suspensions are prepared by passage of spleens through a steel mesh into BSS and are subsequently washed twice with BSS. Further manipulations of spleen cells, labeling of P815 target cells with Cr, mechanics of the assay, and the calculation of results from the CTL assay are known and described in U.S. Pat. No. 4,749,710, incorporated herein by reference. Cytotoxic T lymphocyte activity is determined individually on spleen cells from each animal in each group and the results are expressed as the mean CTL activity (as percent specific Cr release) of each group±the standard deviation.

The results show that mice immunized with P815 cells developed substantial CTL activity within 10 days in the vehicle control groups. A statistically significant reduction in CTL activity is seen in both tests in those groups which were treated with 1α-OH-25-ene-$D_2$, thus documenting the immunosuppressive activity of the compound when administered to animals.

The foregoing examples demonstrate that compounds of the present invention are of value as therapeutic agents while being substantially less toxic than 1α,25-$(OH)_2$-vitamin $D_3$ and 1α-OH-vitamin $D_3$. It is to be understood that although the foregoing examples detail the use of specific 1α-OH-25-ene-D compounds, other compounds within the scope of the claims may be readily utilized in the treatment of this invention with essentially equivalent results.

In summary, the present invention provides 1α-OH-25-ene-D compounds and therapeutic methods for their use in certain diseases and disorders while having significantly less resultant hypercalcemia and hyperphosphatemia.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation that lawfully can be accorded the appended claims.

What is claimed is:

1. A method of achieving an effect in a patient comprising administering an effective amount of a vitamin D compound which is represented by formula (I):

D-Z   (I)

wherein the effect is treating or preventing bone loss or bone mineral content, hyperparathyroidism, cellular hyperproliferation, or modulating immune and inflammatory response or inflammatory response, and wherein D is $D^1$, $D^2$ or $D^3$ moiety in which $D^1$ is a 1α-hydroxyvitamin D moiety, $D^2$ is a 1α-hydroxyprevitamin D moiety and $D^3$ is a 1α-hydroxycholesterol moiety or a 1α-hydroxyergosterol moiety and Z is a C-17 side chain which is a saturated or unsaturated, substituted or unsubstituted, straight-chain or branched $C_4$–$C_8$ hydrocarbon group in which the C-24 or equivalent position is bonded by a single C—C bond to a lower alkyl, lower fluoroalkyl, lower alkenyl or lower fluoroalkenyl, and in which the C-25 or equivalent position has a double bond.

2. The method of claim 1, wherein said 1α-hydroxyvitamin D compound is a compound of formula (II):

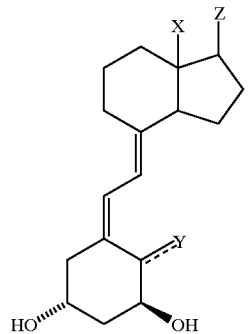

(II)

wherein Y is a methylene group if the bond to Y is a double bond or a methyl group or hydrogen if the bond to Y is a single bond; and X is hydrogen, lower alkyl or lower fluoroalkyl.

3. The method according to claim 2, wherein said 1α-hydroxyvitamin D compound is 1α-hydroxy-25-ene-$D_2$; 1α-hydroxy-25-ene-$D_4$; 1α-hydroxy-25-oxo-$D_2$; or 1α-hydroxy-25-oxo-$D_4$.

4. The method of claim 1, wherein said 1α-hydroxyvitamin D is a compound of formula (IIA):

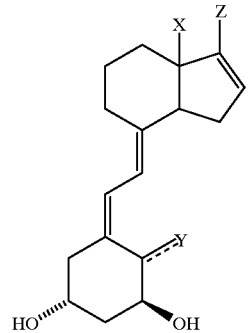

(IIa)

wherein Y is a methylene group if the bond to Y is a double bond or is a methyl group or hydrogen if the bond to Y is a single bond; and X is hydrogen, lower alkyl or lower fluoroalkyl.

5. The method of claim 1, wherein said 1α-hydroxyprevitamin D compound is a compound of formula (III):

(III)

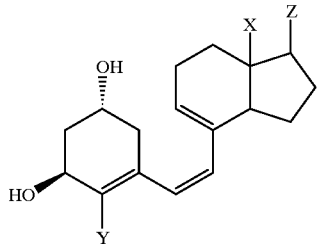

wherein X is hydrogen, lower alkyl or lower fluoroalkyl; and Y is hydrogen or a methyl group.

6. The method of claim 1, wherein Z is a side chain represented by formula (VA):

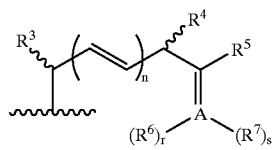

(VA)

wherein n is an integer which is 1 or 2; $R^3$ is hydrogen, lower alkyl, lower fluoroalkyl, lower alkenyl and lower fluoroalkenyl; $R^4$ and $R^5$ are independently lower alkyl, lower fluoroalkyl, lower alkenyl or lower fluoroalkenyl; A is carbon, oxygen, sulfur or nitrogen; r and s are 1 when A is carbon; r is 1 and s is zero when A is nitrogen; r and s are zero where A is oxygen or sulfur; and $R^6$ and $R^7$ are independently hydrogen, lower alkyl, lower fluoroalkyl, lower alkenyl or lower fluoroalkenyl.

7. The method of claim 1, wherein Z is a side chain represented by formula (VC):

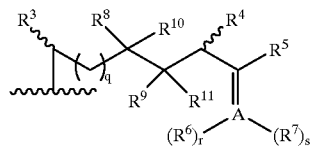

(VC)

wherein a dotted line along the side chain represents an optional additional C—C bond; q is zero or an integer which is 1 or 2; $R^3$ is hydrogen, lower alkyl, lower fluoroalkyl, lower alkenyl or lower fluoroalkenyl; $R^4$ and $R^5$ are independently lower alkyl, lower fluoroalkyl, lower alkenyl or lower fluoroalkenyl; A is carbon, oxygen, sulfur or nitrogen; r is 1 and s is zero when A is nitrogen; r and s are 1 when A is carbon; r and s are zero when A is sulfur or oxygen; and $R^6$ and $R^7$ independently are hydrogen, lower alkyl, lower alkenyl, lower fluoroalkyl or lower fluoroalkenyl.

8. A method of achieving an effect in a patient comprising administering an effective amount of a vitamin D compound which is represented by formula (I):

D-Z (I)

wherein the effect is increasing or maintaining bone mass or bone mineral content, lowering or maintaining lowered parathyroid hormone level, inhibiting hyperproliferative effects, inducing or enhancing cell differentiation modulating immune response, and modulating inflammatory response, and wherein D is $D^1$, $D^2$ or $D^3$ moiety in which $D^1$ is a 1α-hydroxyvitamin D moiety, $D^2$ is a 1α-hydroxyprevitamin D moiety and $D^3$ is a 1α-hydroxycholesterol moiety or a 1α-hydroxyergosterol moiety and Z is a C-17 side chain which is a saturated or unsaturated, substituted or unsubstituted, straight-chain or branched $C_4$–$C_{18}$ hydrocarbon group in which the C-24 or equivalent position is bonded by a single C—C bond to a lower alkyl, lower fluoroalkyl, lower alkenyl or lower fluoroalkenyl, and in which the C-25 or equivalent position has a double bond.

9. The method of claim 8, wherein said vitamin D compound is a compound of formula (II):

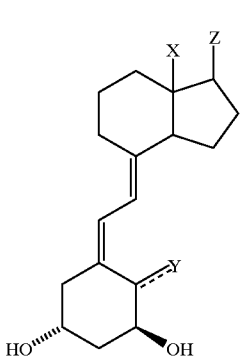

(II)

or of formula (III):

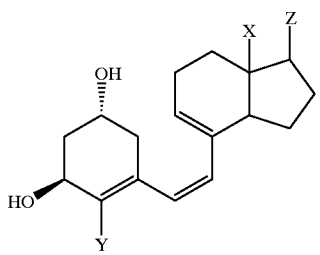

(III)

wherein X is a hydrogen, lower alkyl or lower fluoroalkyl; and Y is a methylene group if the bond to Y is a double bond or is a methyl group or hydrogen if the bond to Y is a single bond; and wherein Z is a side chain of formula (VA):

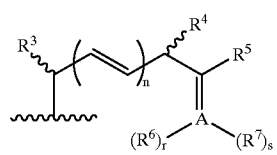

(VA)

wherein n is an integer which is 1 or 2; $R^3$ is hydrogen, lower alkyl, lower fluoroalkyl, lower alkenyl or lower fluoroalkenyl; $R^4$ and $R^5$ are independently lower alkyl, lower fluoroalkyl, lower alkenyl or lower fluoroalkenyl; A is carbon, oxygen, sulfur or nitrogen; r is 1 and s is zero when A is nitrogen; r and s are 1 when A is carbon; r and s are zero when A is sulfur or oxygen; and $R^6$ and $R^7$ are independently hydrogen, lower alkyl, lower alkenyl, lower fluoroalkyl or lower fluoroalkenyl; or of formula (VC):

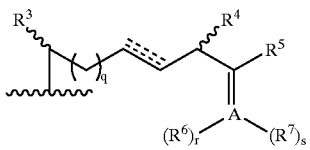

(VC)

wherein a dotted line along the side chain represents an optional additional C—C bond; q is zero or an integer which is 1 or 2; $R^3$ is hydrogen, lower alkyl, lower fluoroalkyl, lower alkenyl or lower fluoroalkenyl; $R^4$ and $R^5$ are independently lower alkyl, lower fluoroalkyl, lower alkenyl or lower fluoroalkenyl; A is carbon, oxygen, sulfur or nitrogen; r is 1 and s is zero when A is nitrogen; r and s are 1 when A is carbon; r and s are zero when A is sulfur or oxygen; and $R^6$ and $R^7$ are independently hydrogen, lower alkyl, lower alkenyl, lower fluoroalkyl or lower fluoroalkenyl.

10. A method of treating a human to alleviate the pathological effects of osteoporosis, hyperparathyroidism, psoriasis, skin cancer, breast cancer, colon cancer, prostate cancer, prostatic hyperplasia and impaired immune response, wherein the method comprises administering to the human a vitamin D compound which is represented by formula (I):

D-Z    (I)

wherein the effect is treating or preventing bone loss or bone mineral content, hyperparathyroidism, cellular hyperproliferation, or modulating immune and inflammatory response or inflammatory response, wherein D is $D^1$, $D^2$ or $D^3$ moiety in which $D^1$ is a 1α-hydroxyvitamin D moiety, $D^2$ is a 1α-hydroxyprevitamin D moiety and $D^3$ is a 1α-hydroxycholesterol moiety or a 1α-hydroxyergosterol moiety and Z is a C-1 7 side chain which is a saturated or unsaturated, substituted or unsubstituted, straight-chain or branched $C_4$–$C_{18}$ hydrocarbon group in which the C-24 or equivalent position is bonded by a single C—C bond to a lower alkyl, lower fluoroalkyl, lower alkenyl or lower fluoroalkenyl, and in which the C-25 or equivalent position has a double bond.

11. A pharmaceutical composition comprising an effective amount of a 1α-hydroxyvitamin D compound which is represented by formula (I):

D-Z    (I)

wherein the effect is treating or preventing bone loss or bone mineral content, hyperparathyroidism, cellular hyperproliferation, or modulating immune and inflammatory response or inflammatory response, wherein D is $D^1$, $D^2$ or $D^3$ moiety in which $D^1$ is a 1α-hydroxyvitamin D moiety, $D^2$ is a 1α-hydroxyprevitamin D moiety and $D^3$ is a 1α-hydroxycholesterol moiety or a 1α-hydroxyergosterol moiety and Z is a C-17 side chain which is a saturated or unsaturated, substituted or unsubstituted, straight-chain or branched $C_4$–$C_{18}$ hydrocarbon group in which the C-24 or equivalent position is bonded by a single C—C bond to a lower alkyl, lower fluoroalkyl, lower alkenyl or lower fluoroalkenyl, and in which the C-25 or equivalent position has a double bond, and a pharmaceutically acceptable carrier, adjuvant or vehicle.

12. The composition of claim 11, wherein the composition is orally administrable.

13. The composition of claim 11, wherein said vitamin D compound is presented in a dosage of 3.5 μg to about 1000 μg/week.

14. The method of claim 1, wherein said vitamin D compound is administered in combination with a bone agent, a cytotoxic agent, an immuno response regulating agent, an antiinflammatory agent or combinations thereof.

15. The method of claim 14, wherein said bone agent is other vitamin D compounds, conjugated estrogens, sodium fluorides, biphosphonates, cobalamin, calcium receptor agonists, pertussin toxin, boron or DHEA.

16. A 1α-hydroxyvitamin D compound which is a compound of formula (II):

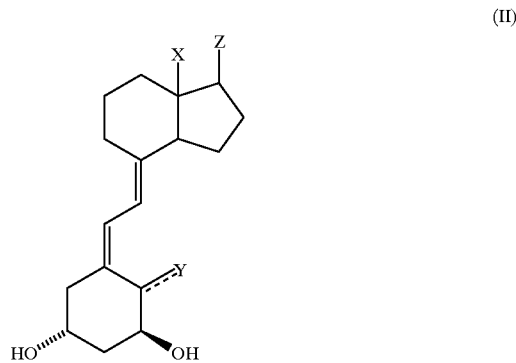

(II)

or a compound of formula (III):

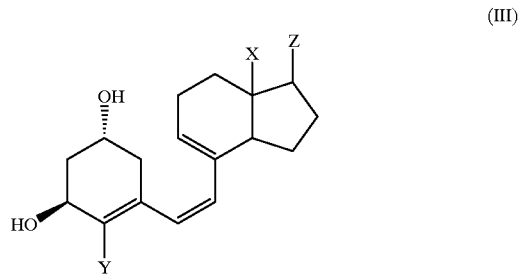

(III)

wherein Z is a C-17 side chain which is a saturated or unsaturated, substituted or unsubstituted, straight-chain or branched $C_4$–$C_{18}$ hydrocarbon group in which the C-24 or equivalent position is bonded by a single C—C bond to a lower alkyl, lower fluoroalkyl, lower alkenyl or lower fluoroalkenyl, and in which the C-25 or equivalent position has a double bond; Y is a methylene group if the bond to Y is a double bond or a methyl group or hydrogen if the bond to Y is a single bond; and X is hydrogen, lower alkyl or lower fluoroalkyl.

17. The compound of claim 16, wherein Z is a side chain of formula (VA):

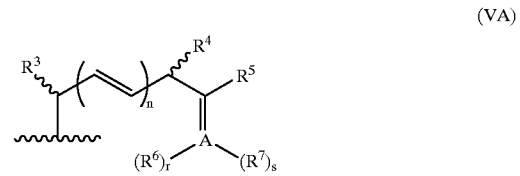

(VA)

wherein n is an integer which is 1 or 2; $R^3$ is hydrogen, lower alkyl, lower fluoroalkyl, lower alkenyl or lower fluoroalkenyl; $R^4$ and $R^5$ are independently lower alkyl, lower fluoroalkyl, lower alkenyl or lower fluoroalkenyl; A is carbon, oxygen, sulfur or nitrogen; r is 1 and s is zero when A is nitrogen; r and s are 1 when A is carbon; r and s are zero when A is sulfur or oxygen; and $R^6$ and $R^7$ are independently hydrogen, lower alkyl, lower alkenyl, lower fluoroalkyl or lower fluoroalkenyl; or of formula (VC):

(VC)

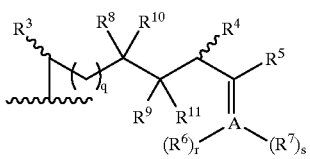

wherein a dotted line along the side chain represents an optional additional C—C bond; q is zero or an integer which is 1 or 2; $R^3$ is hydrogen, lower alkyl, lower fluoroalkyl, lower alkenyl or lower fluoroalkenyl; $R^4$ and $R^5$ are independently lower alkyl, lower fluoroalkyl, lower alkenyl or lower fluoroalkenyl; A is carbon, oxygen, sulfur or nitrogen; r is 1 and s is zero when A is nitrogen; r and s are 1 when A is carbon; r and s are zero when A is sulfur or oxygen; and $R^6$ and $R^7$ are hydrogen, lower alkyl, lower alkenyl, lower fluoroalkyl or lower fluoroalkenyl.

18. A 1α,24-dihydroxyvitamin D compound which is a compound of formula (II):

(II)

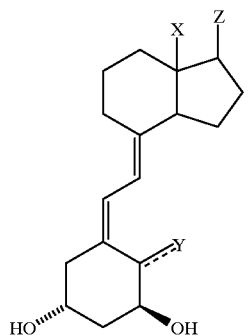

or a compound of formula (III):

(III)

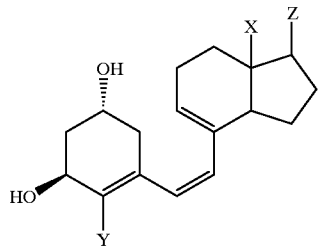

or a compound of formula (IV):

(IV)

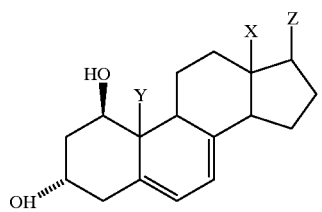

wherein Z is a side chain of formula (VE):

(VE)

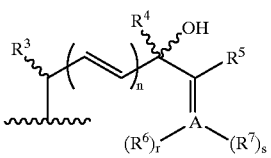

wherein n is an integer which is 1 or 2; $R^3$ is hydrogen, lower alkyl, lower fluoroalkyl, lower alkenyl or lower fluoroalkenyl; $R^4$ and $R^5$ are independently lower alkyl, lower fluoroalkyl, lower alkenyl or lower fluoroalkenyl; A is carbon, oxygen, sulfur or nitrogen; r is 1 and s is zero when A is nitrogen; r and s are 1 when A is carbon; r and s are zero when A is sulfur or oxygen; and $R^6$ and $R^7$ are hydrogen, lower alkyl, lower alkenyl, lower fluoroalkyl or lower fluoroalkenyl; or of formula (VF):

(VF)

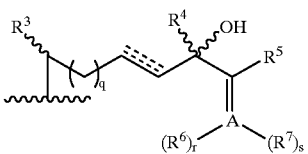

wherein q is zero or an integer which is 1 or 2; $R^3$ is hydrogen, lower alkyl, lower fluoroalkyl, lower alkenyl or lower fluoroalkenyl; $R^4$ and $R^5$ are independently lower alkyl, lower fluoroalkyl, lower alkenyl or lower fluoroalkenyl; A is carbon, oxygen, sulfur or nitrogen; r is 1 and s is zero when A is nitrogen; r and s are 1 when A is carbon; r and s are zero when A is sulfur or oxygen; $R^6$ and $R^7$ independently are hydrogen, lower alkyl, lower alkenyl, lower fluoroalkyl or lower fluoroalkenyl.

19. The compound of claim 18, wherein Z is a side chain of formula (VG):

(VG)

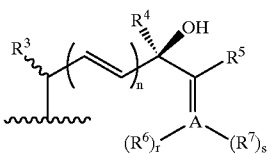

or of formula (VH):

(VH)

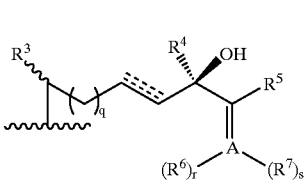

* * * * *

UNITED STATES PATENT AND TRADEMARK OFFICE
CERTIFICATE OF CORRECTION

PATENT NO.    : 5,972,917
DATED         : October 26, 1999
INVENTOR(S)   : Charles W. Bishop et al.

It is certified that error appears in the above-identified patent and that said Letters Patent is hereby corrected as shown below:

Title page,
Item [54], "1 α-HYDROXY-25-ENE-VITAMIN D, ANALOGS AND USES THEREOF" should read -- 1α-HYDROXY-25-ENE-VITAMIN D, ANALOGS AND USES THEREOF --.
After Item [76], Inventors, please add the following:

-- [73]  Assignee: Bone Care International, Inc., Madison, WI (US) --.

Column 1,
Line 1, "1 α-HYDROXY-25-ENE-VITAMIN D, should read -- 1α-HYDROXY-25-ENE-VITAMIN D, --.

Column 3,
Line 40, "$C_1$-$C_8$" should read -- $C_1$-$C_{18}$ --.

Column 5,
Line 27, "$C_4$-$C_8$" should read -- $C_4$-$C_{18}$ --.

Column 8,
Line 1, "Preferred" should not start a new paragraph.
Lines 45-51, formula (VF), should read as follows:

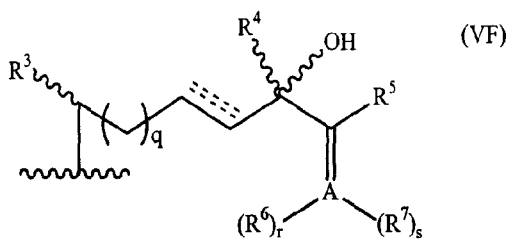

Column 18,
Line 44, "150-300 µg/mL." should read -- 150-300 pg/mL. --.

UNITED STATES PATENT AND TRADEMARK OFFICE
CERTIFICATE OF CORRECTION

PATENT NO.   : 5,972,917
DATED        : October 26, 1999
INVENTOR(S)  : Charles W. Bishop et al.

It is certified that error appears in the above-identified patent and that said Letters Patent is hereby corrected as shown below:

Column 20,
Line 2, "$C_4$-$C_8$" should read -- $C_4$-$C_{18}$ --.

Column 21,
Lines 40-47, formula (VC), should read as follows:

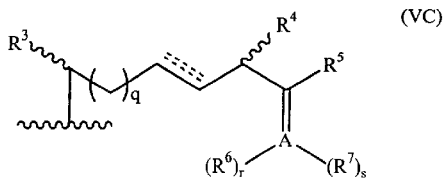

Column 24,
Lines 52-57, formula (VA), should read as follows:

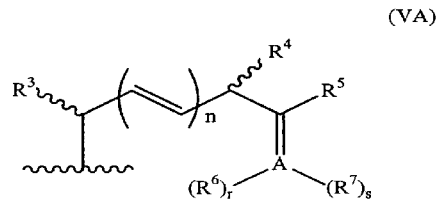

Signed and Sealed this

Twentieth Day of May, 2003

JAMES E. ROGAN
*Director of the United States Patent and Trademark Office*

UNITED STATES PATENT AND TRADEMARK OFFICE
CERTIFICATE OF CORRECTION

PATENT NO.   : 5,972,917
DATED        : October 26, 1999
INVENTOR(S)  : Charles W. Bishop, Joyce C. Knutson and Stephen Strugnell It is certified that error appears in the above-identified patent and that said Letters Patent is hereby corrected as shown below:

Column 25,
Lines 1-10, formula (VC), should read as follows:

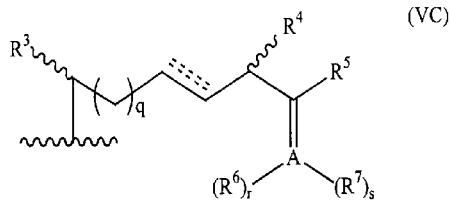

(VC)

Signed and Sealed this

Second Day of March, 2004

JON W. DUDAS
*Acting Director of the United States Patent and Trademark Office*